(12) United States Patent
Liu

(10) Patent No.: US 9,402,421 B2
(45) Date of Patent: *Aug. 2, 2016

(54) ELECTRONIC CIGARETTE

(71) Applicant: Qiuming Liu, Shenzhen (CN)

(72) Inventor: Qiuming Liu, Shenzhen (CN)

(73) Assignee: HUIZHOU KIMREE TECHNOLOGY CO., LTD., SHENZHEN BRANCH, Shenzhen, Guangdong Province (CN)

( * ) Notice: Subject to any disclaimer, the term of this patent is extended or adjusted under 35 U.S.C. 154(b) by 461 days.

This patent is subject to a terminal disclaimer.

(21) Appl. No.: 14/118,227

(22) PCT Filed: Mar. 29, 2013

(86) PCT No.: PCT/CN2013/073473
§ 371 (c)(1),
(2) Date: Nov. 16, 2013

(87) PCT Pub. No.: WO2014/153778
PCT Pub. Date: Oct. 2, 2014

(65) Prior Publication Data
US 2014/0290677 A1    Oct. 2, 2014

(51) Int. Cl.
*A24F 47/00* (2006.01)
*A61M 15/06* (2006.01)

(52) U.S. Cl.
CPC .............. *A24F 47/008* (2013.01); *A61M 15/06* (2013.01)

(58) Field of Classification Search
None
See application file for complete search history.

(56) References Cited

U.S. PATENT DOCUMENTS

| 5,147,582 A * | 9/1992 | Holzner, Sr. ............ A61L 9/122 239/60 |
| 6,443,146 B1 * | 9/2002 | Voges .................... A23F 47/002 128/200.14 |
| 2013/0180533 A1 * | 7/2013 | Kim ....................... A24F 47/008 131/273 |
| 2013/0192615 A1 * | 8/2013 | Tucker ................... H01C 17/00 131/328 |

* cited by examiner

*Primary Examiner* — Michael H Wilson
*Assistant Examiner* — Eric Yaary
(74) *Attorney, Agent, or Firm* — Cheng-Ju Chiang

(57) ABSTRACT

The invention is related to an electronic cigarette, including an atomizing device with a tobacco-liquid cup, and a battery electrically connected with the atomizing device, herein, the tobacco-liquid cup forms a recessed cavity, the battery is received in the cavity. The battery of the present invention is set in the atomizing device, so that the whole length of the electronic cigarette is effectively reduced, and it is more convenient to take the electronic cigarette.

12 Claims, 8 Drawing Sheets

ELECTRONIC CIGARETTE

CROSS REFERENCE TO RELATED APPLICATIONS

The present application is a 35 U.S.C. §371 National Phase conversion of International (PCT) Patent Application No. PCT/CN2013/073473, filed on Mar. 29, 2013, the disclosure of which is incorporated by reference herein. The PCT International Patent Application was filed in Chinese.

BACKGROUND OF THE INVENTION

1. Field of the Invention

The present invention relates to an electronic cigarette, especially to the electronic cigarette with a battery being fitted in an atomizing device thereof.

2. Related Art

An existing electronic cigarette comprises an atomizing device and a battery, the battery is set to one end of the atomizing device and electrically connected with the atomizing device, such configuration results a longer cigarette body, and inconvenient carrying.

SUMMARY OF THE INVENTION

An object of the present invention is to provide an electronic cigarette in a proper whole length and being easily carried.

To achieve the above object, an electronic cigarette of the present invention, comprises an atomizing device with a tobacco-liquid cup, and a battery electrically connected with the atomizing device; herein the tobacco-liquid cup defines a recessed cavity, and the battery is arranged in the recessed cavity.

Furthermore, the tobacco-liquid cup comprises an outer cup body and an inner cup body, a first end of the inner cup body and the outer cup body are tightly connected so that the inner cup body and the outer cup body enclose a liquid-storing space, and the inner cup body is hollow to form the recessed cavity for receiving the battery.

Furthermore, the tobacco-liquid cup is set with a mouthpiece near a second end of the inner cup body; the mouthpiece through its center defines an inhaling port to communicate with an air passageway for vapor mist to be drawn therethrough; the atomizing device further comprises an atomizer disposed between the mouthpiece and the battery to vaporize tobacco liquid into vapor mist.

Furthermore, the atomizer comprises an electric heat wire; the second end of the inner cup body is set with a first electrode assembly which is electrically connected with the electric heat wire and the battery; the first electrode assembly comprises a first seat and a first terminal post both of which are insulated from each other and respectively electrically connected to both ends of the electric heat wire to form positive and negative electrodes of the atomizer.

Furthermore, the battery rod is fitted outside of the battery; one end of the battery rod abutting against the first electrode assembly is set with a second electrode assembly coupled to the first electrode assembly; the second electrode assembly comprises a second seat and a second terminal post both of which are insulated from each other and respectively connected to positive and negative poles of the battery.

Furthermore, the battery rod and the tobacco-liquid cup are detachably connected.

Furthermore, the tobacco-liquid cup is set with a first magnetic part where the tobacco-liquid cup is interconnected with the battery rod; the battery rod is correspondingly set with a second magnetic part drawing the first magnetic part so that the tobacco-liquid cup and the battery rod are tightly interconnected.

Furthermore, the first seat is made from conductive magnet or magnetic materials to form the first magnetic part, or the first electrode assembly is set with a separate component made from magnet or magnetic materials to form the first magnetic part; the second seat is made from conductive magnet or magnetic materials to form the second magnetic part, or the second electrode assembly is set with a separate component made from magnet or magnetic materials to form the second magnetic part.

Furthermore, the first end of the inner cup body is tightly connected with the outer cup body by a end cap; the end cap is made from magnet or magnetic materials to form the first magnetic part, or the end cap is set with a separate component made from magnet or magnetic materials to form the first magnetic part; the battery rod is set with a battery cover away from the atomizer for enclosing the battery; the battery cover is made from magnet or magnetic materials to form the second magnetic part, or the battery cover is set with a separate component made from magnet or magnetic materials to form the second magnetic part.

Furthermore, the second seat is hollow and tubular, its end facing the battery defines an accommodating cavity for receiving the second terminal post; the second terminal post is fixed in the accommodating cavity by means of an insulation sleeve.

Furthermore, the insulation sleeve comprises a first insulation support and a second insulation support both of which are interconnected and define an inner chamber; the second terminal post is elastically fitted in center of the insulation sleeve by means of a compression spring fixed in the inner chamber; both the first insulation support and the second insulation support axially define a first terminal hole and a second terminal hole in their opposite end walls to communicate with the inner chamber for both ends of the second terminal post extending therethrough; the second terminal post forms a blocking ring in the inner chamber; the compression spring has both ends thereof respectively abutting against the blocking ring and an inner wall of the second insulation support, therefore, one end of the second terminal post facing the first electrode assembly remains extending outwards.

Furthermore, the atomizer is arranged between the mouthpiece and the first seat via a support; the support is hollow and tubular, its center forms an atomizing chamber to communicate with the air passageway and receive the atomizer.

Furthermore, the atomizer further comprises a liquid-delivery rod with both ends thereof extending into the tobacco-liquid cup to absorb tobacco liquid; the electric heat wire winds round the liquid-delivery rod; the support defines openings radially through its side wall for fitting the liquid-delivery rod.

Furthermore, one end of the first seat extends into the support to form a brace tightly fitted with the first seat; a sealing bush is set where the mouthpiece and the support are connected.

Furthermore, the outer cup body is partly or wholly transparent or semitransparent.

The present invention has advantages as: the tobacco-liquid cup defines a recessed cavity, and the battery is received in the recessed cavity, the whole length of the cigarette is effectively reduced, therefore, the electronic cigarette is more conveniently taken and used; magnetic parts are set where the tobacco-liquid cup and the battery-rod are interconnected so as to impart a magnetic connection therebetween, via which assembly and disassemble thereof are convenient, and it is convenient to replace the battery as well. The tobacco-liquid cup is transparent or semitransparent, the reminder of tobacco liquid in the tobacco-liquid cup can be observed any time, thereby tobacco liquid can be refilled in time.

Embodiments of the present invention will now be further described in detail with reference to the attached Figures.

DESCRIPTION OF THE PREFERRED EMBODIMENTS

Figure 1:
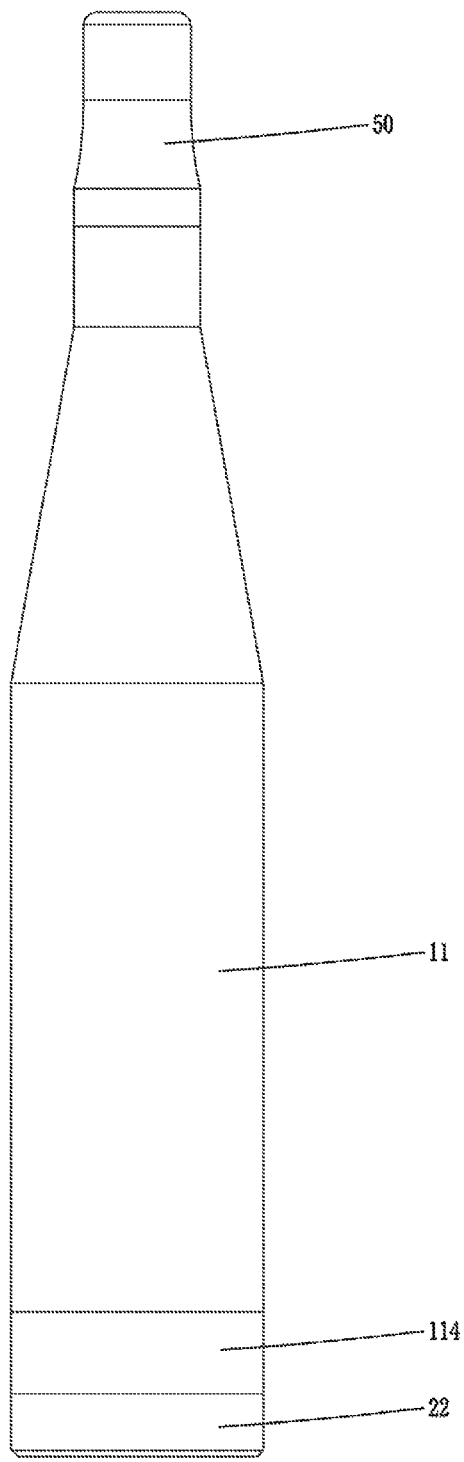
FIG. 1 is a front view of an electronic cigarette in accordance with an embodiment of the present invention.

As shown in FIGS. 1 to 8, an electronic cigarette in accordance with embodiments of the present invention, comprises an atomizing device 10 for vaporizing tobacco-liquid into vapor mists, and a battery 20 which is electrically connected with the atomizing device 10 so as to supply power source for the atomizing device 10.

The atomizing device 10 comprises a tobacco-liquid cup 11 and an atomizer 12 fixed in the tobacco-liquid cup 11.

The tobacco-liquid cup 11 is used for storing tobacco liquid and configured as main body of the electronic cigarette in accordance with this embodiment, and has one end defined a recessed cavity 111; the battery 20 is received in the cavity 111.

Figure 6:
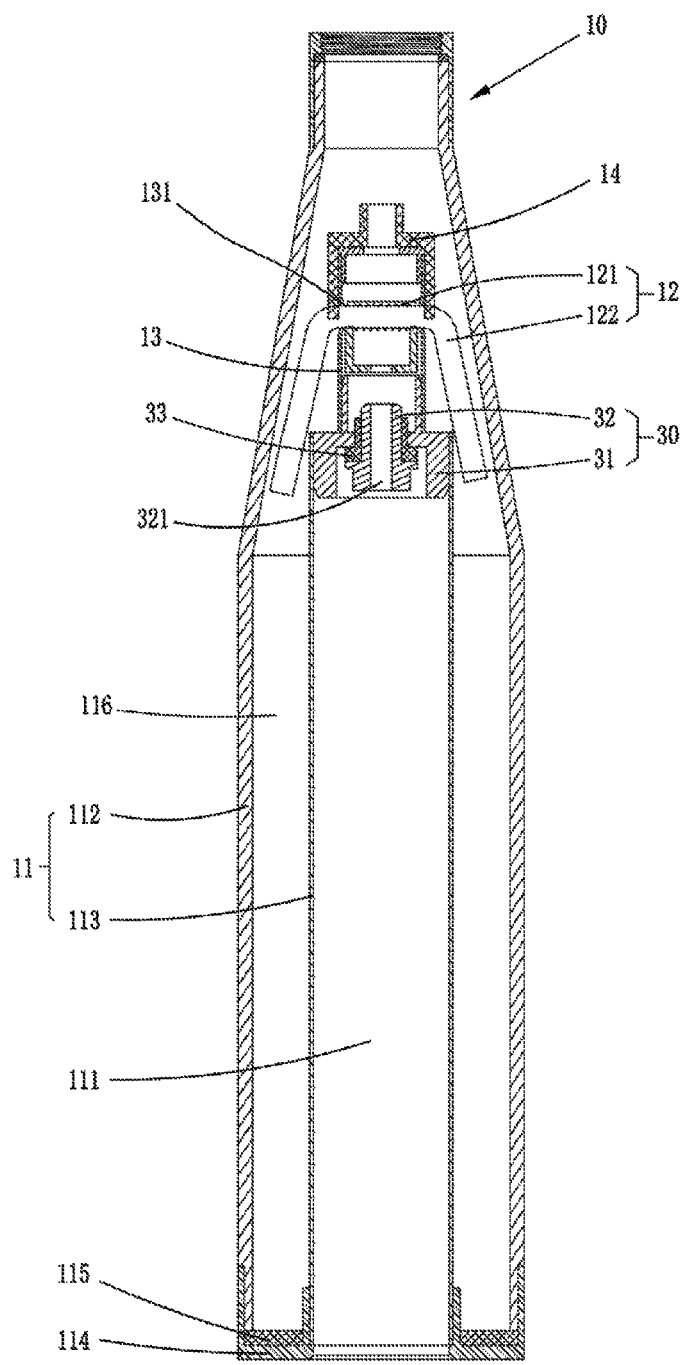
FIG. 6 is a cross-sectional view of an atomizing device in accordance with an embodiment of the present invention.

Specifically, as shown in FIG. 6, the tobacco-liquid cup 11 comprises an outer cup body 112 and an inner cup body 113. Both the outer cup body 112 and inner cup body 113 are hollow and tubular. The inner cup body 113 is set in the outer cup body 112 with the first end thereof tightly connected with the outer cup body 112 and the second end unconnected with the outer cup body 112 so as to form an opening for filling tobacco liquid, the annular space enclosed between the two cup bodies 112 and 113 forms a liquid-storing space 116, and the inner cup body 113 has its hollow part configured as the cavity 111 for receiving the battery 20.

The outer cup body 112 and the inner cup body 113 are separately set in accordance this embodiment, the first end of the inner cup body 113 is tightly connected with the outer cup body 112 by an end cap 114. The end cap 114, the outer cup body 112 and the inner cup body 113 are tightly fitted among the three, and a first seal ring 115 is placed at their connection to ensure a tight connection therebetween. As one embodiment, the first end of the inner cup body 113 and the corresponding end of the outer cup body 112 may also be manufactured in-mold.

The atomizer 12 comprises an electric heat wire 121 and a liquid-delivery rod 122, and the electric heat wire 121 winds round the liquid-delivery rod 122. The electric heat wire 121 is electrically connected with the battery 20, so as to vaporize tobacco liquid into vapor mist after a supply of electricity thereto. The liquid-delivery rod 122 is made from glass fiber or other high temperature resistant fiber, and is used for absorbing and delivering tobacco liquid for the electric heat wire 122 hearting.

The second end of the inner cup body 113 is set with a first electrode assembly 30, the first electrode assembly 30 is electrically connected both ends of the electric heat wire 121 as positive and negative electrodes of the atomizer 12, and is further electrically connected with positive and negative poles of the battery 20.

Specifically, as shown in FIGS. 2 to 6, the first electrode assembly 30 comprises a first seat 31 and a first terminal post 32, both the first seat 31 and the first terminal post 32 are made from metal conductive materials, and insulation is obtained by setting a first insulation sleeve 33 between the two. The first seat 31 and the first terminal post 32 are respectively electrically connected both ends of the electric heat wire 121 so as to form the positive and negative electrodes of the atomizer 12.

The first seat 31 is hollow in accordance with this embodiment, the first terminal post 32 is tightly fitted in the first seat 31 and insulated from the first seat 31 in use of the first insulation sleeve 33. The first terminal post 32 is hollow as well, and its hollow center forms a first air inlet port 321 for environmental air to enter the atomizing device 10.

Figure 7:
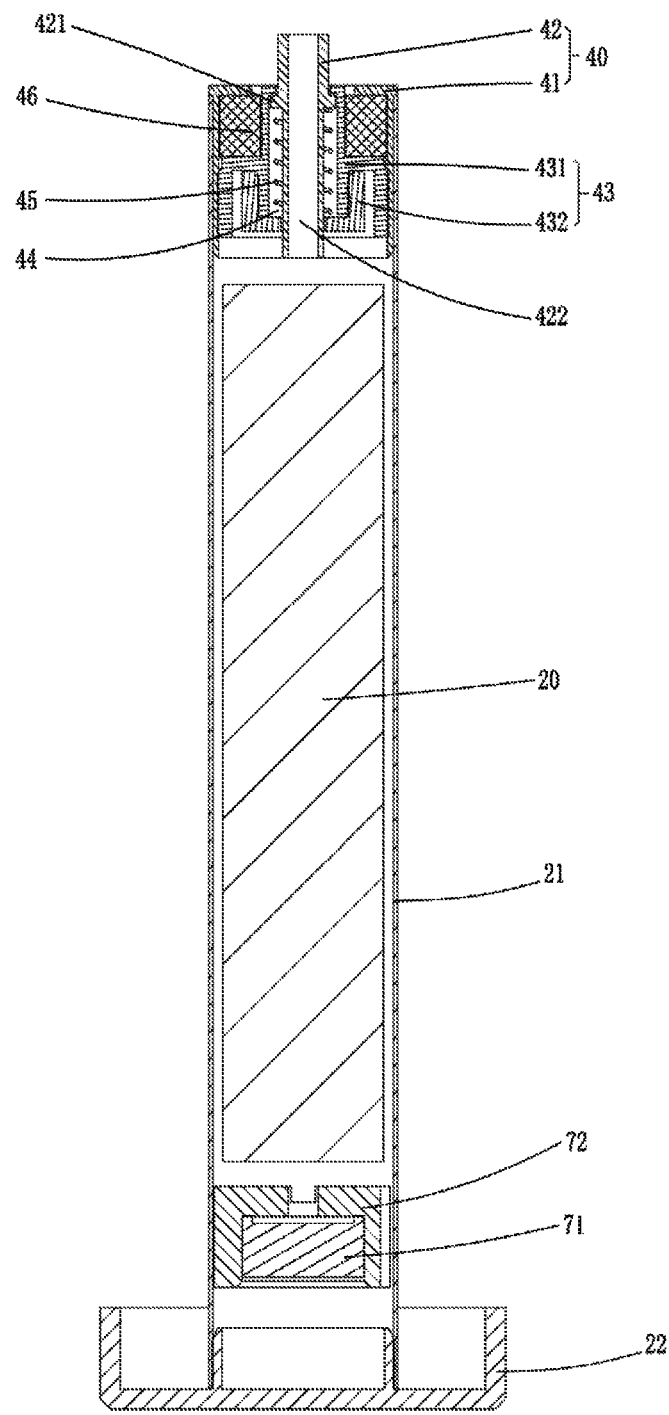
FIG. 7 is a cross-sectional view of a battery rod in accordance with the first embodiment of the present invention.
Figure 8:
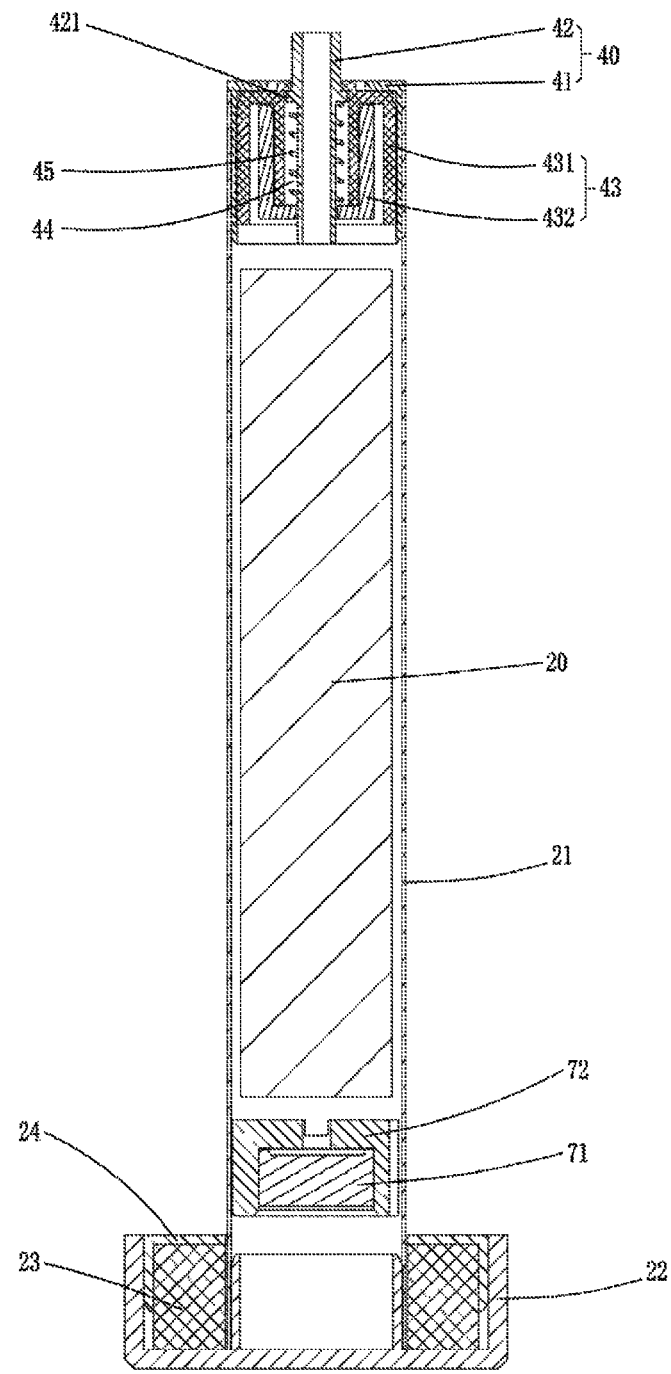
FIG. 8 is a cross-sectional view of a battery rod in accordance with the second embodiment of the present invention.

Referring to FIGS. 7 and 8, outside of the battery 20 is fitted with a battery rod 21. One end of the battery rod 21 contacting the first electrode assembly 30 is set with a second electrode assembly 40, and the second electrode assembly 40 is coupled to the first electrode assembly 30, via which the battery 20 and the atomizing device 10 are electrically connected.

Moreover, the other end of the battery rod 21 is set with a battery cover 22, via which the battery 20 is enclosed in the battery rod 21. The battery cover 22 and the end cap 114 have coupled periphery in accordance with this embodiment, and while the battery rod 21 is placed in the cavity 111, the battery cover 22 and the end cap 114 abut against each other with their peripheries aligned.

Figure 2:
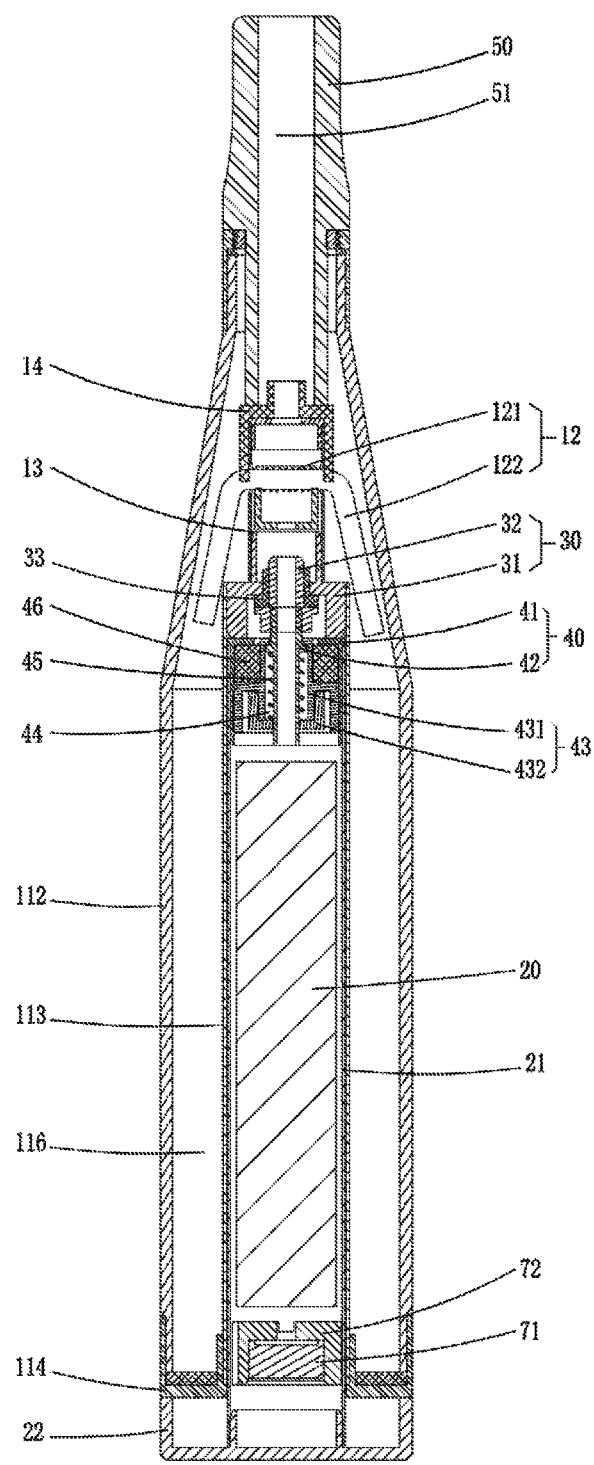
FIG. 2 is a cross-sectional view of the electronic cigarette in accordance with the first embodiment of the present invention.

Referring to FIGS. 2, 7, 8, the second electrode assembly 40 comprises a second seat 41 and a second terminal post 42 insulated from each other; the second seat 41 and the second terminal post 42 are made from metal conductive materials, and correspondingly connected with positive and negative electrodes of both the battery 20 and the atomizer 12. The second seat 41 and the second terminal post 42 are set with a second insulation sleeve 43 therebetween, and retain insulated from each other in use of the second insulation sleeve 43.

Referring to FIGS. 7 and 8, the second seat 41 is hollow as well; its end facing the battery 20 defines an accommodating cavity for receiving the second terminal post 42. The second insulation sleeve 43 comprises a first insulation support 431 and a second insulation support 432; the first insulation support 431 and the second insulation support 432 are interconnected, and are tightly fitted in the accommodating cavity of the second seat 41. The first insulation support 431 and the second insulation support 432 are internally coupled so as to define an inner chamber 44, and the second terminal post 42 is elastically fitted in center of the second insulation sleeve 43 by means of a compression spring 45 fixed in the inner chamber 44. Both the first insulation support 431 and the second insulation support 432 have their opposite end walls axially defined a first terminal hole and a second terminal hole to communicate the inner chamber 44 for both ends of the second terminal post 42 extending outwards therefrom. The second terminal post 42 forms a blocking ring 421 in the inner chamber 44, and the compression spring 45 has both ends thereof respectively abutting against the blocking ring 421 and an inner wall of the second insulation support 432, so that the end of the second terminal post 42 facing the first electrode assembly 30 remains extending outwards. The second terminal post 42 is hollow as well, and defines a second air inlet port 422 through its center to communicate with the first air inlet port 321 so that an air passageway is connected.

When assembling the electronic cigarette, the power rod 21 is inserted in the recessed cavity 111 of the inner cup body 113; the first seat 31 and the second seat 41 abut against each other; the first terminal post 32 and the second terminal post 42 abut against each other; the second terminal post 42 is pushed by the first terminal post 32, overcomes the elastic force from the compress spring 45, then goes forward to the battery 20 and finally is tightly fitted between the first terminal post 32 and the battery 20, therefore, the second terminal post 42 is well electrically connected with the first terminal post 32 and the battery 20. When the first electrode assembly 30 is separated from the second electrode assembly 40, the external force is removed from the second terminal post 42, thus the compression spring 45 restores the second terminal post 42.

Figure 4:
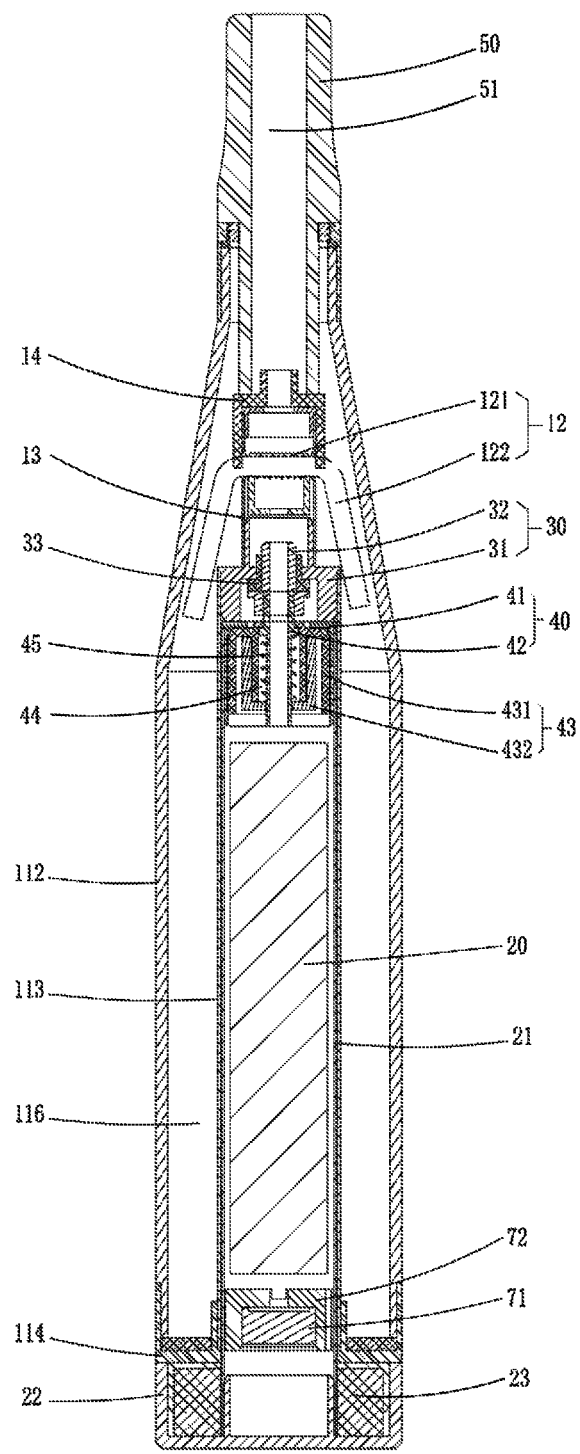
FIG. 4 is a cross-sectional view of the electronic cigarette in accordance with the second embodiment of the present invention.
Figure 5:
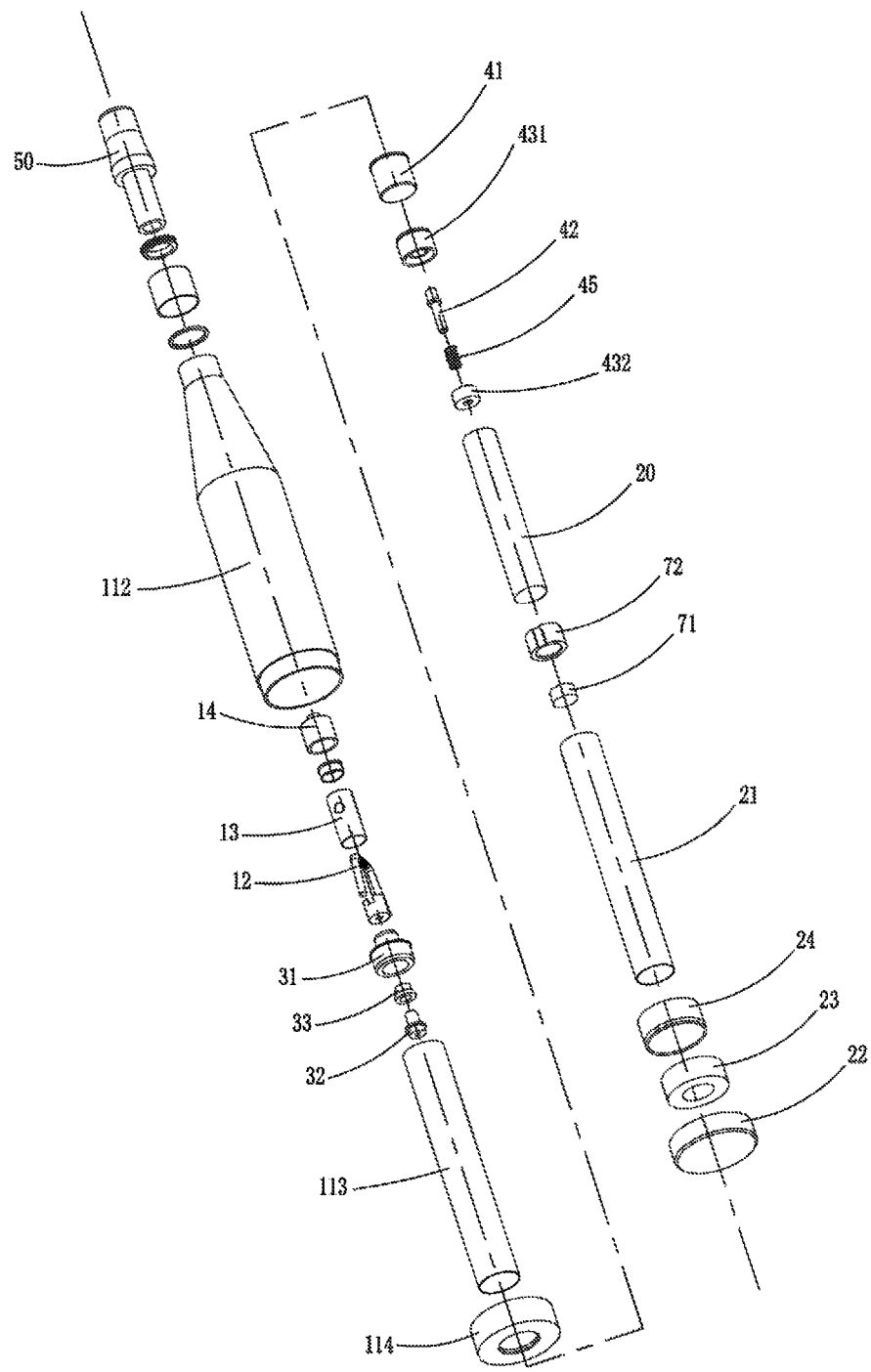
FIG. 5 is an exploded view of the electronic cigarette in accordance with the second embodiment of the present invention.

The tobacco-liquid cup 11 is detachably connected with the battery rod 21 in accordance with this embodiment. As shown in FIGS. 2 and 4, the tobacco-liquid cup 11 and the battery rod 21 is preferably magnetically connected. Specifically, the tobacco-liquid cup 11 is set with a first magnetic part where it connects the battery rod 21; the battery rod 21 is correspondingly set with a second magnetic part for attracting the first magnetic part so that the tobacco-liquid cup 11 and the battery rod 21 are tightly interconnected.

The first electrode assembly 30 is set at one end of the tobacco-liquid cup 11 near the battery 2, the second electrode assembly 40 is set at one end of the battery 20 near the atomizing device 10, and the first electrode assembly 30 and the second electrode assembly 40 are coupled. Therefore, When the first and second magnetic parts are designed, considering to reduce components and to simplify the structure of the electronic cigarette, the first seat 31 may be directly made from conductive magnet or magnetic materials so as to form the first magnetic part, or the first electrode assembly 30 is set with an separate component made from magnet or magnetic materials as the first magnetic part; accordingly, the second seat 41 may be directly made from conductive magnet or magnetic materials so as to be used as the second magnetic part, or the second electrode assembly 40 is set with an separate component made from magnet or magnetic materials as the second magnetic part.

Figure 3:
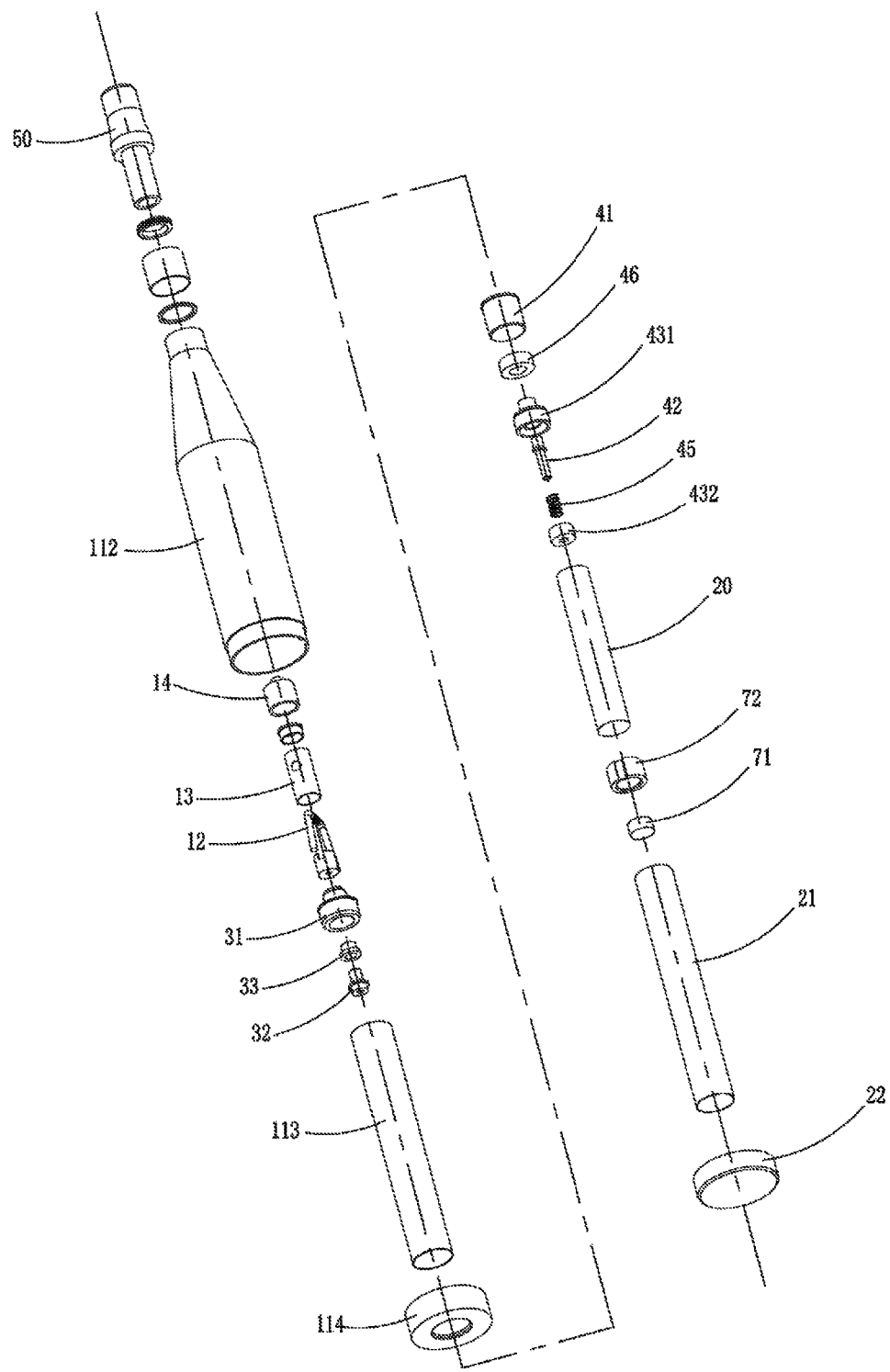
FIG. 3 is an exploded view of the electronic cigarette in accordance with the first embodiment of the present invention.

In accordance with the embodiment as shown in FIGS. 2 and 3, the first magnetic part is the first seat 31 from metal conductive materials, while the second magnetic part is a first permanent magnet 46 in the second seat 41. Referring to FIG. 7, the first permanent magnet 46 has an annular shape, and is fitted round an end of the first insulation support 431 facing the first seat 31.

In accordance with another embodiment, the first magnetic part and the second magnetic part may also be configured at the other connecting ends of the tobacco-liquid cup 11 and the battery rod 21, that is, the end cap 114 is made from magnet or magnetic materials so as to form the first magnetic part, or the end cap 114 is set with an separate component made from magnet or magnetic materials as the first magnetic part; accordingly, the battery cover 22 is made from magnet or magnetic materials so as to form the second magnetic part, or the battery cover 22 is set with an separate component made from magnet or magnetic materials as the second magnetic part.

In accordance with the embodiment as shown in FIGS. 3 and 4, the end cap 114 is made from metal as the first magnetic part, while the battery cover 22 is set with a second permanent magnet 23 as the second magnetic part; or the end cap 114 is set with an separate component made from magnet or magnetic materials as the first magnetic part; the second permanent magnet 23 has an annular shape as well, and is mounted in the battery cover 22 by a tightening cap 24.

It is understood that the tobacco-liquid cup 11 and the batter rod 21 may be interconnected by a thread connection, clamping means or the like; for instance, the end cap 114 and the battery cover 22 are correspondingly set with outer threads and inner threads at their joining position to form a thread connection therebetween.

As shown in FIGS. 1 to 5, the tobacco-liquid cup 11 is set with a mouthpiece 50 at its end away from the battery 20, and the mouthpiece 50 defines an inhaling port 51 along its center and communicating with the air passageway for vapor mist being drawn therethrough.

Referring to FIGS. 2, 4, 6, the atomizer 12 is fixed between the mouthpiece 50 and the first seat 31 by a support 13. The support 13 is hollow and tubular, and defines an atomizing chamber in its center for communicating with the air passageway and receiving the atomizer 12.

The atomizer 12 is radially fitted in the atomizing chamber; the liquid-delivery rod 122 has both ends thereof extending outwards the atomizing chamber to the tobacco-liquid cup 11 so as to absorb the tobacco liquid, the support 13 radially defines openings 131 through its sidewall for fitting the liquid-delivery rod 122.

The support 13 is rested on the first seat 31 in accordance with this embodiment, one end of the first seat 31 abutting against the support 13 extends into the support 13 to form a brace, and the support 13 is tightly fitted round the brace. The other end of the support 13 is fitted with a sealing bush 14; the sealing bush 14 has one end thereof tightly abutting against the liquid-delivery rod 122, and has the other end thereof extending into the mouthpiece 50 to form a protrusion; the mouthpiece 50 has one end thereof fitted round the protrusion and tightly abutting against the sealing bush 14, so that the tobacco-liquid cup 11 is internally sealed by means of the sealing bush 14, therefore, tobacco liquid in the tobacco-liquid cup 11 is prevented from leaking from the inhaling port 51. The sealing bush 14 correspondingly defines a through hole along its center to communicate with both the atomizing chamber and the inhaling port 51 so as to connect the air passageway.

Meanwhile, for observing the remaining tobacco liquid in the liquid-storing space 116 and filling tobacco liquid in time so that the electronic cigarette is regularly used, the outer cup body 112 is partly or wholly configured to be transparent or semitransparent in accordance with this embodiment.

As shown in FIGS. 2 to 5, the battery rod 21 has an atomizing control unit therein, the atomizing control unit is respectively electrically connected with the battery 20 and the atomizing device 10 so as to control the atomizing device 10 powered on or off. The atomizing control unit may be set between the atomizing device 10 and the battery 20, or be set at one end of the battery 20 away from the atomizing device 10.

The atomizing control unit is preferably set at the end of the battery 20 away from the atomizing device 10 in accordance with this embodiment, and comprises an atomizing control circuit and an atomizing control switch which is connected with the atomizing control circuit.

The atomizing control switch is a sensor switch 71 in accordance with this embodiment; and the sensor switch 71 is mounted in the battery rod 21 by means of a switch holder 72. Specifically, the sensor switch 71 is a capacitive sensor switch, when the user smokes in use of the electronic cigarette, the capacitive sensor switch senses the inhaling air flow and thereafter its electric capacity is changed, which controls the atomizing control circuit to switch on the power supply, and thus the electronic cigarette starts work. As an embodiment, the sensor switch 71 may be an airflow sensor switch, when the user inhales by the mouthpiece 50; a negative pressure is generated in the electronic cigarette, thus the air sensor switch produces pulsing signals, which controls the atomizing control circuit to switch on the power supply.

Because the sensor switch 71 itself is accurately manufactured, and it generally has a special built-in controller, the atomizing control circuit may be directly integrated into the controller of the sensor switch 71 in accordance with this embodiment. As an embodiment, the atomizing control circuit may also be integrated to a sensor control circuit board which is separately set outside of the sensor switch 71 and respectively electrically connected with the sensor switch 71 and the battery 20.

As an embodiment, the atomizing control switch may also be a traditional key switch, the key switch is electrically connected with the battery 20 by means of a key control circuit board so that the atomizing control circuit is controlled by key operations for electrically connecting or disconnecting the atomizing device 10.

Still referring to FIGS. 2 to 5, the end of the battery rod 21 near the battery cover 22 is further set with a light device; the light device is used as a working indicator of the electrode cigarette, and has a light emitting unit electrically connected with the battery 20. The light emitting unit is a red lighter in accordance with this embodiment, when the user smoke by the electronic cigarette, the end of the electronic cigarette away from the mouthpiece 50 forms red light ring like a cigarette burning, which improves a real visual sense of the user. The battery cover 22 is set with a transparent or semitransparent light cap at its end for the light emitting unit to send out light. As an embodiment, the battery cover 22 may also be wholly transparent or semitransparent.

It is understood that, the electronic cigarette in accordance with the embodiments of the present invention is not limited to such embodiments as shown in FIGS. 1 to 8, and various technical characteristics of each embodiment may be combined each other to form new embodiments.

While the embodiments of the present invention have been illustrated and described, it will be understood that various amendments and modifications can be made by those skilled in the art without departing from the principle and the spirit of the present invention, and those amendments and modifications shall also be deemed in the scope of the invention.

What is claimed is:

1. An electronic cigarette, comprising an atomizing device with a tobacco-liquid cup, and a battery electrically connected with the atomizing device; wherein the tobacco-liquid cup defines a recessed cavity, and the battery is arranged in the recessed cavity; wherein the tobacco-liquid cup comprises an outer cup body and an inner cup body, a first end of the inner cup body and the outer cup body are tightly connected whereby the inner cup body and the outer cup body enclose a liquid-storing space, and the inner cup body is hollow to form the recessed cavity for receiving the battery; wherein the tobacco-liquid cup is set with a mouthpiece near a second end of the inner cup body; the mouthpiece through its center defines an inhaling port to communicate with an air passageway for vapor mist being drawn therethrough; the atomizing device further comprises an atomizer disposed between the mouthpiece and the battery to vaporize tobacco liquid into vapor mist; wherein the atomizer comprises an electric heat wire; the second end of the inner cup body is set with a first electrode assembly which is electrically connected with the electric heat wire and the battery; the first electrode assembly comprises a first seat and a first terminal post both of which are insulated from each other and respectively electrically connected with both ends of the electric heat wire to form positive and negative electrodes of the atomizer.

2. The electronic cigarette of claim 1, wherein the battery rod is fitted outside of the battery; one end of the battery rod abutting against the first electrode assembly is set with a second electrode assembly coupled to the first electrode assembly; the second electrode assembly comprises a second seat and a second terminal post both of which are insulated from each other and respectively connected with positive and negative poles of the battery.

3. The electronic cigarette of claim 2, wherein the battery rod and the tobacco-liquid cup are detachably connected.

4. The electronic cigarette of claim 3, wherein the tobacco-liquid cup is set with a first magnetic part where the tobacco-liquid cup is interconnected with the battery rod; the battery rod is correspondingly set with a second magnetic part drawing the first magnetic part whereby the tobacco-liquid cup and the battery rod are tightly interconnected.

5. The electronic cigarette of claim 4, wherein the first seat is made from conductive magnet or magnetic materials to form the first magnetic part, or the first electrode assembly is set with a separate component made from magnet or magnetic materials to form the first magnetic part; the second seat is made from conductive magnet or magnetic materials to form the second magnetic part, or the second electrode assembly is set with a separate component made from magnet or magnetic materials to form the second magnetic part.

6. The electronic cigarette of claim 4, wherein the first end of the inner cup body is tightly connected with the outer cup body by a end cap; the end cap is made from magnet or magnetic materials to form the first magnetic part, or the end cap is set with a separate component made from magnet or magnetic materials to form the first magnetic part; the battery rod is set with a battery cover away from the atomizer for enclosing the battery; the battery cover is made from magnet or magnetic materials to form the second magnetic part, or the battery cover is set with a separate component made from magnet or magnetic materials to form the second magnetic part.

7. The electronic cigarette of claim 2, wherein the second seat is hollow and tubular, its end facing the battery defines an accommodating cavity for receiving the second terminal post; the second terminal post is fixed in the accommodating cavity by means of an insulation sleeve.

8. The electronic cigarette of claim 7, wherein the insulation sleeve comprises a first insulation support and a second insulation support both of which are interconnected and define an inner chamber; the second terminal post is elastically fitted in center of the insulation sleeve by means of a compression spring fixed in the inner chamber; both the first insulation support and the second insulation support axially define a first terminal hole and a second terminal hole in their opposite end walls to communicate with the inner chamber for both ends of the second terminal post extending therethrough; the second terminal post forms a blocking ring in the inner chamber; the compression spring has both ends thereof respectively abutting against the blocking ring and an inner wall of the second insulation support, whereby one end of the second terminal post facing the first electrode assembly remains extending outwards.

9. The electronic cigarette of claim 4, wherein the atomizer is arranged between the mouthpiece and the first seat via a support; the support is hollow and tubular, its center forms an atomizing chamber to communicate with the air passageway and receive the atomizer.

10. The electronic cigarette of claim 9, wherein the atomizer further comprises a liquid-delivery rod with both ends thereof extending into the tobacco-liquid cup to absorb tobacco liquid; the electric heat wire winds round the liquid-delivery rod; the support defines openings radially through its side wall for fitting the liquid-delivery rod.

11. The electronic cigarette of claim 9, wherein one end of the first seat extends into the support to form a brace tightly fitted with the first seat; a sealing bush is set where the mouthpiece and the support are connected.

12. The electronic cigarette of claim 2, wherein the outer cup body is partly or wholly transparent or semitransparent.

* * * * *